US008288040B2

(12) United States Patent
Muldoon et al.

(10) Patent No.: US 8,288,040 B2
(45) Date of Patent: Oct. 16, 2012

(54) HIGH VOLTAGE ELECTROLYTE

(75) Inventors: John Muldoon, Saline, MI (US); Gary Allred, Wake Forest, NC (US); Scott Ankeney, Ann Arbor, MI (US); Masaki Matsui, Ann Arbor, MI (US); Anthony Dotse, Cary, NC (US); Tsuyoshi Sugimoto, Toyota (JP)

(73) Assignees: Toyota Motor Engineering & Manufacturing North America, Inc., Erlanger, KY (US); Toyota Motor Corporation, Toyota (JP); Synthonix Corporation, Wake Forest, NC (US)

( * ) Notice: Subject to any disclaimer, the term of this patent is extended or adjusted under 35 U.S.C. 154(b) by 702 days.

(21) Appl. No.: 12/371,979

(22) Filed: Feb. 17, 2009

(65) Prior Publication Data

US 2010/0209780 A1 Aug. 19, 2010

(51) Int. Cl.
*H01M 6/16* (2006.01)

(52) U.S. Cl. ........ 429/339; 429/341; 429/200; 429/199; 429/330; 429/340; 429/307; 429/188; 429/329; 252/62.2; 252/364

(58) Field of Classification Search .................. 429/339, 429/341, 200, 199, 330, 340, 307, 188, 329; 252/62.2, 364
See application file for complete search history.

(56) References Cited

U.S. PATENT DOCUMENTS

| 7,223,502 | B2 | 5/2007 | Onuki |
| 2004/0038133 | A1 | 2/2004 | Yamaguchi et al. |
| 2007/0224514 | A1 | 9/2007 | Kotato et al. |
| 2009/0011340 | A1 | 1/2009 | Lee et al. |

FOREIGN PATENT DOCUMENTS

| JP | 11-195430 | * | 7/1999 |
| JP | 2006-221972 | | 8/2006 |
| KP | 10-2003-0065407 | | 8/2003 |
| KP | 10-0507591 | | 8/2005 |

OTHER PUBLICATIONS

Chen, Renjie et al., "Binary Complex Electrolytes Based on $LiX[X=N(SO^2CF^3)2, CF_3SO_3, ClO_4]$-Acetamide for Electric Double Layer Capacitors", Journal of the Electrochemical society, 154 (7), 2007, pp. 703-708.

Zu, Bin et al., "Room temperature molten salt as electrolyte for carbon nanobute-based electric double layer capacitors", Journal of Power Sources, 158, 2006, pp. 773-778.

Zhang, Sheng Shui, "A review on electrolyte additives for lithium-ion batteries", Journal of Power Sources, 162 (2006), pp. 1379-1394.

* cited by examiner

*Primary Examiner* — Laura Weiner
(74) *Attorney, Agent, or Firm* — Gifford, Krass, Sprinkle, Anderson & Citkowski, P.C.

(57) ABSTRACT

A battery that includes a cathode, anode and an electrolytic solution containing an organic electrolyte solvent including a compound of the formula: $R_1$—CO—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolyte is stable at voltages of greater than 4.0 volts.

26 Claims, 3 Drawing Sheets

HIGH VOLTAGE ELECTROLYTE

FIELD OF THE INVENTION

The invention relates to organic electrolyte solvents, organic electrolytic solutions utilizing the organic electrolyte solvents, and batteries utilizing the electrolytic solutions.

BACKGROUND OF THE INVENTION

It is generally known in the art to utilize various organic solvents as electrolytes for chargeable lithium type batteries. Various electrolytes include materials such as carbonates and cyclic esters as well as ethers. However, these conventional organic solvents are prone to decomposition during the cycling of a charge and discharge of a battery.

Additionally, conventional organic solvent type electrolytes are prone to failure at high operating voltages such as greater than 4.0 volts. Such electrolytes may also be prone to thermal failure at elevated temperatures. Failures may result in reduced cycle life and decreased safety of batteries using such electrolytes. There is therefore a need in the art for an improved electrolytic solution that is stable at high voltages and at elevated temperatures. There is also a need in the art for an improved electrolytic solution that improves the cycle life and safety of a battery incorporating the electrolytic solution.

SUMMARY OF THE INVENTION

In one aspect there is disclosed an organic electrolyte solvent that includes a compound of the formula: $R_1$—CO—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolyte solvent is stable at voltages of greater than 4.0 volts.

In another aspect there is disclosed an organic electrolytic solution that includes an organic electrolyte solvent that includes a compound of the formula: $R_1$—CO—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolytic solution is stable at voltages of greater than 4.0 volts.

In a further aspect there is disclosed a battery that includes a cathode, anode and electrolytic solution that includes an organic electrolyte solvent including a compound of the formula: $R_1$—CO—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives wherein the electrolytic solution is stable at voltages of greater than 4.0 volts.

DETAILED DESCRIPTION OF THE PREFERRED EMBODIMENTS

Figure 1:
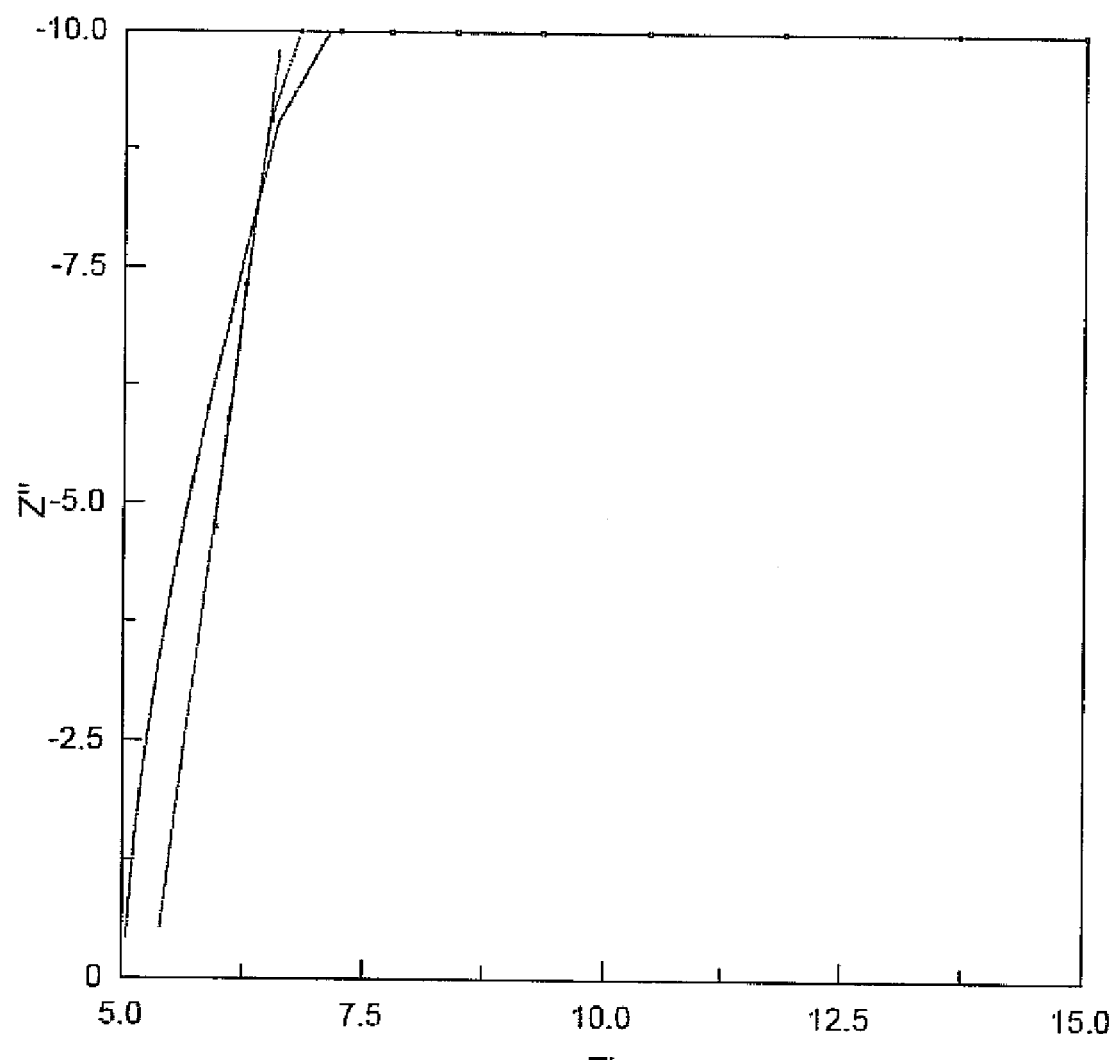
FIG. 1 is a plot of an impedance profile at room temperature for a 1 molar lithium salt dissolved in the electrolyte of the invention in comparison to a 1 molar lithium salt dissolved in a carbonate based electrolyte.

In one aspect there is disclosed an organic electrolyte solvent that includes a compound of the formula: $R_1$—CO—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives. The organic electrolyte solvent remains stable at voltages of greater than 4.0 volts. In another aspect, $R_1$, $R_2$ and $R_3$ may be selected from linear alkyl, branched allyl, partially fluorinated alkyl and fully fluorinated alkyl groups having from 1 to 5 carbons. In a preferred aspect, $R_2$ and $R_3$ may include a methyl moiety.

In another aspect, there is disclosed an organic electrolytic solution that includes the organic electrolyte solvent that includes a compound of the formula: $R_1$—CO—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives. Additionally, an electrolyte salt may be dissolved in the organic electrolyte wherein the electrolytic solution remains stable at voltages of greater than 4.0 volts. The perfluorinated analogues may be synthesized by electrochemical fluorination (ECF) or direct fluorination of a desired substrate.

Various electrolyte salts may include lithium salts that are generally used in the field. In one aspect, lithium salts may be selected from the group consisting of: $LiPF_6$, $LiAsF_6$, $LiSbF_6$, $LiBF_4$, $LiClO_4$, $LiCF_3SO_3$, $Li(CF_3SO_2)_2N$, $Li(C_2F_5SO_2)_2N$, $LiC_4F_9SO_3$, $Li(CF_3SO_2)_3C$, $LiBPh_4$, LiBOB, and $Li(CF_3SO_2)(CF_3CO)N$ and combinations thereof. The organic electrolyte solution may include the electrolyte salts in a concentration of from 0.5 molar to 3 molar.

The organic electrolyte solution may also include electrolyte additives selected from solid electrolyte interface (SEI) forming additives, cathode protecting agents, salt stabilizers, overcharge protecting additives, lithium depositing additives, salvation enhancers, as well as corrosion inhibitors and wetting agents.

In one aspect, the SEI forming additives may be utilized to improve the formation of an SEI layer on the surface of an anode of a battery, as will be discussed in more detail below. In one aspect, the SEI forming additives may be selected from the group consisting of: vinylene carbonate, vinyl ethylene carbonate, ethylene carbonate, allyl ethyl carbonate, vinyl acetate, divinyl adipate, acrylic acid nitrile, 2-vinyl pyridine, maleic anhydride, maleimides, methyl cinnamate, phosphonate, vinyl-containing silane-based compounds, furan derivatives that contain two double bonds in each molecule, sulfur-based compounds, including $SO_2$, polysulfide, cyclic alkyl sulfites, aryl sulfites, nitrates, nitrites, halogenated ethylene carbonate, halogenated lactone, methyl chloroformate, carboxylphenol, aromatic esters, anhydrides, succinimide, N-benzyloxy carbonyloxy succinimide, aromatic isocyanates, $B_2O_3$, organic borates, boroxine compounds, lithium salt-based boron compounds, halogenated organic compounds, polydimethylsiloxane, silanes, tris(pentafluorophenyl) borane, and alkali metal salts.

The cathode protecting agents may also be included in the organic electrolyte solution. The cathode protecting agents may be selected from the group consisting of: amine-based organic bases such as butylamine, carbodiimide based compounds such as N,N-dicyclohexylcarbodiimide, N,N-diethylamino trimethylsilane.

Various salt stabilizers may be utilized in the organic electrolyte solution and may be selected from the group consisting of: LiF, Lewis bases including tris(2,2,2-trifluoroethyl) phosphate, amide-based compounds including 1-methyl-2-pyrrolidinone, fluorinated carbamate and hexamethyl-phosphoramide.

Additionally, overcharge protecting additives may be included in the organic electrolyte solution. In one aspect, the overcharge protecting additives may be selected from the group consisting of: metallocenes, tetracyanoethylene, tetramethylphenylenediamine, dihydrophenazine derivatives bearing either 2-hydroxypropyl or ethyl substituents on both N atoms, substituted aromatic or heterocyclic compounds and their alkali metal salts, anisole-family compounds, 2,5-diterbutyl-1,4-dimethoxybenzene, monomethoxy benzene class compounds, hexaethyl benzene, bipyridyl or biphenyl carbonates, difluoroanisoles, S- or N-containing heterocyclic aromatic compounds such as thianthrene and 2,7-diacetyl thianthrene, phenothiazinebased compounds, lithium fluorododecaborates, xylene, cyclohexylbenzene, biphenyl, 2,2-diphenylpropane, phenyl-tert-butyl carbonate, phenyl-R-phenyl compounds, 3-thiopheneacetonitrile, heterocyclic compounds including furan, thiophene, and N-methylpyrrole, 3,4-ethylenedioxythiophene, and LiBOB.

Various lithium depositing additives may also be included in the organic electrolyte solution. The lithium depositing additives may be selected from the group consisting of: $SO_2$ compounds, polysulfide, water, 2-methyltetrahydrofuran, 2-methylthiophene, nitromethane, tetraalkylammonium chlorides with a long allyl chain, cetyltrimethylammonium chlorides, lithium and tetraethylammonium salts of perfluorooctanesulfonate, perfluoropolyethers, nitrile sucrose, nitrile cellulose, $AlI_3$, SnI, HF, and fluoroethylene carbonate.

Salvation enhancers may also be included in the organic electrolyte solution. Various salvation enhancers include borates, boranes and borole compounds.

In addition, corrosion inhibitors and wetting agents may also be included in the organic electrolyte solution. Various corrosion inhibitors and wetting agents may include agents selected from the group consisting of: LiBOB, LiODFB, ionic and non-ionic surfactants, cyclohexane, trialkyl phosphate, linear esters with high molecular weight including methyl decanoate and dodecyl acetate, tertiary carboxylic acids, and $P_2O_5$.

Additionally, other solvents may be included in the organic electrolyte solution. The additional solvents may include organic carbonates, ionic liquids, silanes and sulfones.

In another aspect, a lithium battery that includes the organic electrolytic solution is described. Generally, the battery may include a positive and negative electrode as well as a separator material and the organic electrolytic solution. Various types of batteries including lithium batteries such as lithium secondary batteries, lithium ion batteries and lithium ion polymer batteries as well as lithium primary batteries may utilize the organic electrolytic solution.

In one aspect, the cathode may include an active material for which absorption and release of various cations of the lithium salts can take place. In one aspect, the active material may include the cations. For example, in a battery that is charged and discharged through the migration of lithium ions such as a lithium ion secondary battery, various lithium composite oxides containing lithium and a transition metal may be utilized. Various examples include composite oxides with the general formula $LiMO_2$ where M can be any metallic elements or combination of metallic elements such as cobalt, aluminum, chromium, manganese, nickel, iron, vanadium, magnesium, titanium, zirconium, niobium, molybdenum, copper, zinc, indium, strontium, lanthanum, and cesium. Additionally, the active material can be made of a material with the chemical formula $LiMn_2O_4$ or a material with the general formula $LiMPO_4$ where M can be any metallic element or combination of elements such as cobalt, aluminum, chromium, manganese, nickel, iron, vanadium, magnesium, titanium, zirconium, niobium, molybdenum, copper, zinc, indium, strontium, lanthanum, and cesium The positive electrode of the battery disclosed may include any of the active materials that may be held on an electrically conductive member that includes metal or another conductive element. Various conductive members including rod-shaped, plate or foil bodies as well as mesh or other type structures. In addition to the active material and electron conducting material various other materials such as binders may also be included. Various binders including polyvinylidene fluoride, polyvinyl diamine fluoride, polytetrafluoroethylene, polyvinyl diamine fluoride, hexafluoropropylene copolymers, styrene butadiene rubber and various other materials may be utilized.

The negative electrode or anode may also include an active material for which absorption and release of the cation described above can take place. Various negative electrode active materials may include a carbon material having an amorphous structure and/or graphite structure. For example, various kinds of active materials commonly utilized in lithium batteries may include natural graphite, mezocarbon microbeads, highly ordered pyrolytic graphite, hard carbon and soft carbon, as well as additional materials. Further, various other active materials that are able to maintain the electric potential of the negative electrode such as lithium titanate may also be utilized. Additionally, elements that can alloy with lithium such as tin, silicon, antimony, bismuth, silver, zinc, aluminum, lead, germanium, arsenic and composite materials containing said elements can be utilized as negative electrode active materials. As with the positive electrode, the negative electrode may include an active material that is held on an electrically conductive member that includes metal or the like. Various structures including plates, rods, foils and other type structures may be utilized. As with the previously described cathode, a binder material may be mixed with the active material as well as other additives such as plasticizers or other such additives to form the negative electrode of the battery.

The battery also includes the electrolytic solution as described above. The electrolytic solution may include an organic electrolyte solvent including a compound of the formula: $R_1$—CO—$NR_2$—$OR_3$ wherein $R_1$ is selected from alkanes, alkenes, alkynes, aryls and their substituted derivatives and perfluorinated analogues; $R_2$ is selected from alkanes, alkenes, alkynes, aryls and their substituted derivatives; $R_3$ is selected from alkanes, alkenes, alkynes, aryls and their substituted derivatives, and an electrolyte salt dissolved in the organic electrolyte wherein the battery is stable at voltages of greater than 4.0 volts.

EXAMPLES

Preparation of 2,2,3,3,3-Pentafluoro-N-methoxy-N-methyl-propionamide

To a 3-neck 1.0-L round-bottomed flask (RBF) equipped with dry ice/liquid nitrogen bath, mechanical stirrer, dry nitrogen gas inlet, thermoprobe, addition funnel, and bubbler were charged with pentafluoropropionic anhydride (50 g, 0.16 moles), N,O-dimethylhydroxylamine hydrochloride (1.03 equivalents) and anhydrous dichloromethane (400 mL). The system was flushed with nitrogen and then cooled to 0° C. While stirring at this temperature, anhydrous pyridine (3.00 equivalents) was added dropwise and the resulting reaction mixture was stirred at 0° C. for 60 min and quenched with water. The layers were separated. The organic layer was washed with water, hydrochloric acid (1 M, 3.00 equivalents), water, and then with brine. The organic solution was then dried over anhydrous $MgSO_4$, filtered and the solvent removed on a rotary evaporator. The residue was re-dissolved in dichloromethane and plugged through a short pad of silica gel, eluting with dichloromethane. Eluents containing pure product were pooled and the solvent evaporated on the rotary evaporator. The resulting oil was pulled under high vacuum for a few hours to obtain product as oil (26.52 g, 79%): $^1$H NMR (400 MHz, $CDCl_3$-d) $\delta$ 3.34 (s, 3H), 3.64 (s, 3H).

The resulting product was tested for ionic conductivity using stainless steel (SUS) blocking electrodes in a coin cell. The ionic conductivity of 1.0M $LiPF_6$ dissolved in the product was studied by AC impedance spectroscopy (FIG. 1) at room temperature. The impedance data shows that organic electrolyte (2,2,3,3,3-Pentafluoro-N-methoxy-N-methyl-propionamide) has similar conductivity to that of organic carbonates.

Figure 2:
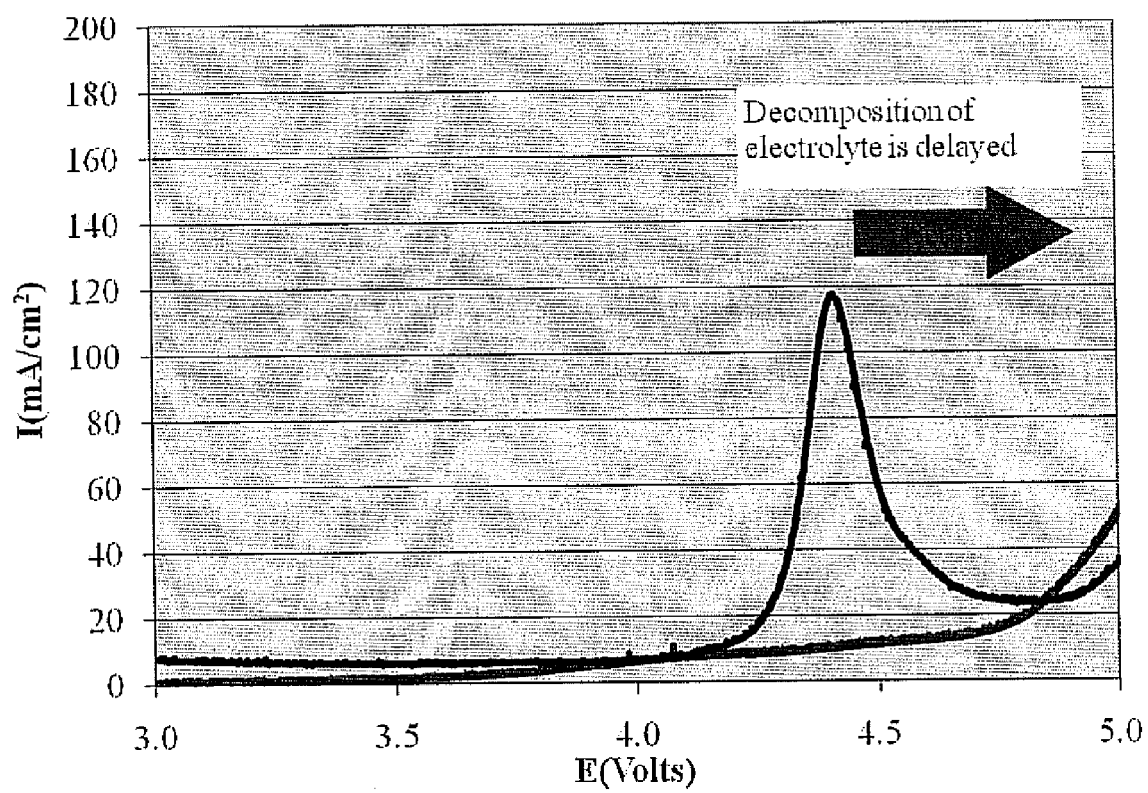
FIG. 2 is a plot of the current as a function of the voltage for the comparative electrolytes of FIG. 1.

Referring to FIG. 2, a cyclic voltametry scan measured in a coin cell containing a SUS vs. Li/Li$^+$ electrode arrangement is presented for the 2,2,3,3,3-Pentafluoro-N-methoxy-N-methyl-propionamide electrolyte and a carbonate based electrolyte. The testing was performed at room temperature at a scan rate of 1 mV/s.

The Voltage stability of the 2,2,3,3,3-Pentafluoro-N-methoxy-N-methyl-propionamide electrolyte with 1M $LiPF_6$ (4.85V vs Li/Li$^+$) is superior to organic carbonates with 1M $LiPF_6$ (4.28V vs Li/Li$^+$).

Additionally, batteries were prepared with the 2,2,3,3,3-Pentafluoro-N-methoxy-N-methyl-propionamide electrolyte for full cells and half cells. For the full cell, a positive electrode was formed by applying an even coating of a mixture containing a lithium transition metal oxide, a conductive carbon additive, and polyvinylidene fluoride (PVDF) as a bonding agent in an 85:10:5 ratio onto a thin aluminum foil current collecting material. A negative electrode was formed by applying an even coating of a mixture of graphitic carbon and PVDF as a bonding agent to a thin copper foil current collecting material. The electrolyte solution contained 1M $LiPF_6$ dissolved in the organic solvent and contains 5% wt ethylene carbonate (EC) and 2% wt vinylene carbonate (VC) as an SEI forming additive. A thin polyolefin material was used as a separator between the two electrodes. Size 2032 coin cells were prepared using these materials and were charged and discharged with a current density of 1 mA/cm$^2$.

For the half cell, a positive electrode was formed by applying an even coating of a mixture containing a lithium transition metal oxide, a conductive carbon additive, and PVDF as a bonding agent in an 85:10:5 ratio onto a thin aluminum foil current collecting material. A negative electrode was formed of a thin foil of lithium metal. The electrolyte solution contained 1M $LiPF_6$ dissolved in the organic solvent and contains 5% wt EC and 2% wt VC as an SEI forming additive. A thin polyolefin material was used as a separator between the two electrodes. Size 2032 coin cells were prepared using these materials and were charged and discharged with a current density of 1 mA/cm$^2$.

Figure 3:
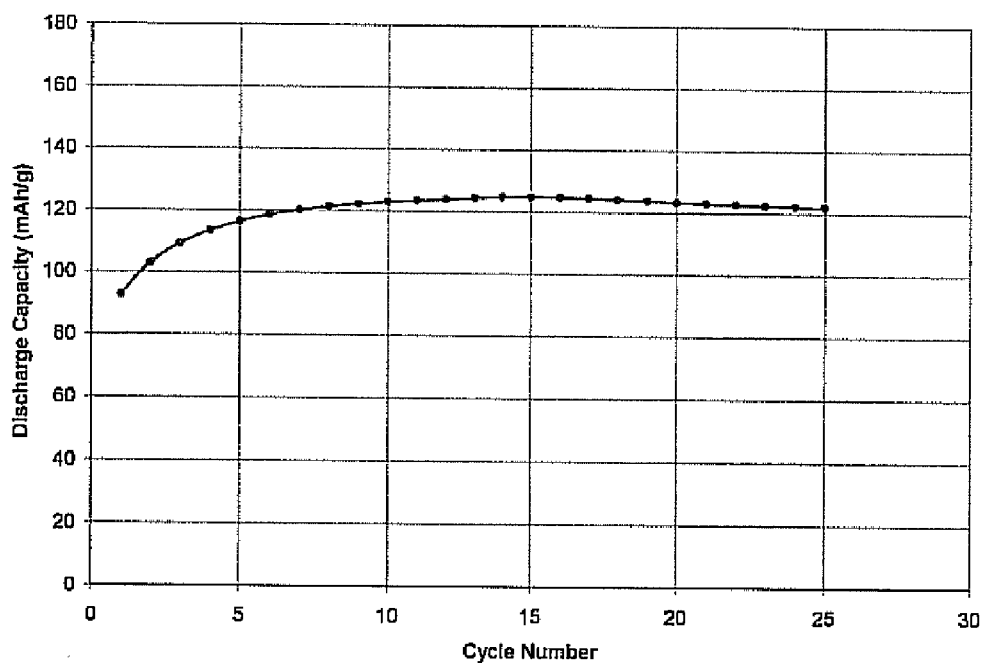
FIG. 3 is a plot of the discharge capacity as a function of cycle number for a battery comprised of a lithium transition metal oxide containing cathode and carbonaceous material anode incorporating the electrolytic solution of the invention.
Figure 4:
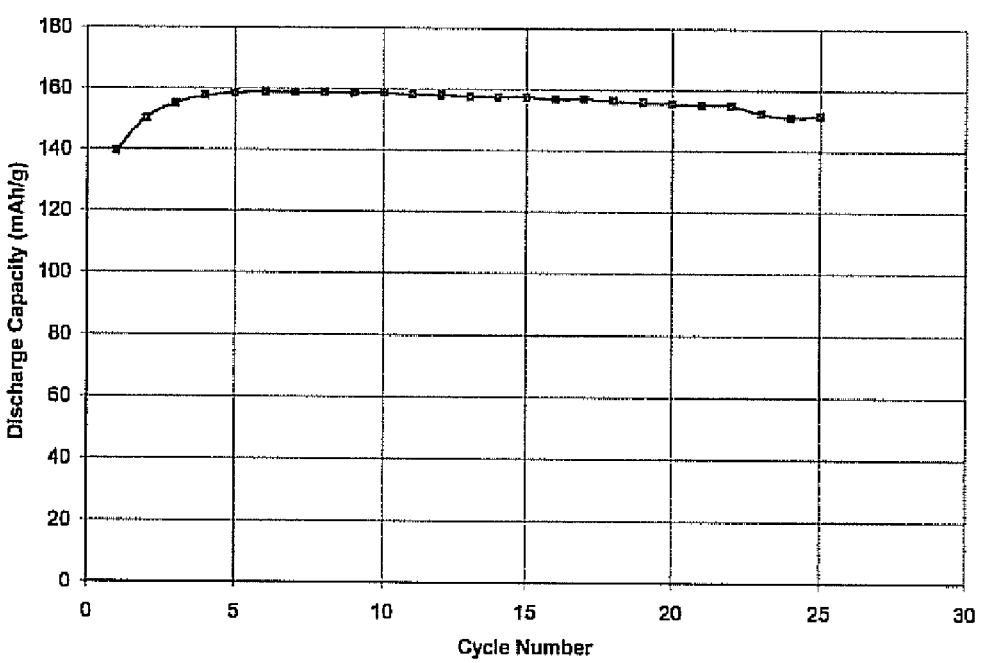
FIG. 4 is a plot of the discharge capacity as a function of cycle number for a battery comprised of a lithium transition metal oxide containing cathode and a lithium metal anode incorporating the electrolytic solution of the invention.

Referring to FIGS. 3 and 4 plots of the discharge capacity as a function of cycle number are shown for the full and half cells. As can be seen from the plots, the discharge capacity of the cells remain stable over many cycles.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

The invention claimed is:
1. An organic electrolyte solvent comprising:
a compound of the formula:

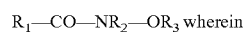

$R_1$—CO—$NR_2$—$OR_3$ wherein $R_1$ is selected from alkyls, alkenyls, alkynyls, aryls and substituted fluorine derivatives that are partially or fully fluorinated of the alkyls, alkenyls, alkynyls and aryls of $R_1$; $R_2$ is selected from alkyls, alkenyls, alkynyls, aryls and substituted fluorine derivatives of the alkyls, alkenyls, alkynyls and aryls of $R_2$; $R_3$ is selected from alkyls, alkenyls, alkynyls, aryls and substituted fluorine derivatives of the alkyls, alkenyls, alkynyls and aryls of $R_3$ wherein when $R_1$, $R_2$, or $R_3$ is an alkyl, the alkyl has from 1 to 5 carbons and wherein the electrolyte solvent is stable at voltages of greater than 4.0 volts.

2. The organic electrolyte solvent of claim 1 wherein $R_1$, $R_2$ and $R_3$ are selected from linear alkyl, branched alkyl, partially fluorinated alkyl, and fully fluorinated alkyl groups.

3. The organic electrolyte solvent of claim 1 wherein $R_2$ comprises a methyl moiety.

4. The organic electrolyte solvent of claim 1 wherein $R_3$ comprises a methyl moiety.

5. An organic electrolytic solution comprising:
an organic electrolyte solvent including a compound of the formula:

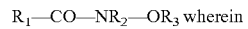

$R_1$—CO—$NR_2$—$OR_3$ wherein $R_1$ is selected from alkyls, alkenyls, alkynyls, aryls and substituted fluorine derivatives that are partially or fully fluorinated of the alkyls, alkenyls, alkynyls and aryls of $R_1$; $R_2$ is selected from alkyls, alkenyls, alkynyls, aryls and substituted fluorine derivatives of the alkyls, alkenyls, alkynyls and aryls of $R_2$; $R_3$ is selected from alkyls, alkenyls, alkynyls, aryls and substituted fluorine derivatives of the alkyls, alkenyls, alkynyls and aryls of $R_3$ wherein when $R_1$, $R_2$ or $R_3$ is an alkyl, the alkyl has from 1 to 5 carbons; and an electrolyte salt dissolved in the organic electrolyte solvent wherein the electrolytic solution is stable at voltages of greater than 4.0 volts.

6. The organic electrolytic solution of claim 5 including additional solvents selected from organic carbonates, ionic liquids, silanes and sulfones.

7. The organic electrolytic solution of claim 5 wherein $R_1$ is a substituted fluorine derivatives of the alkyls, alkenyls, alkynyls and aryls of $R_1$ synthesized by electrochemical fluorination.

8. The organic electrolytic solution of claim 5 wherein R1 is a substituted fluorine derivatives of the alkyls, alkenyls, alkynyls and aryls of $R_1$ synthesized by direct fluorination.

9. The organic electrolytic solution of claim 5 wherein the electrolyte salt is selected from the group consisting of: $LiPF_6$, $LiAsF_6$, $LiSbF_6$, $LiBF_4$, $LiClO_4$, $LiCF_3SO_3$, $Li(CF_3SO_2)_2N$, $Li(C_2F_5SO_2)_2N$, $LiC_4F_9SO_3$, $Li(CF_3SO_2)_3C$, $LiBPh_4$ wherein Ph is phenyl, LiBOB, $Li(CF_3SO_2)(CF_3CO)N$ and combinations thereof.

10. The organic electrolytic solution of claim 9 wherein the electrolyte salt has a concentration of from 0.5M to 3.0M.

11. The organic electrolyte solution of claim 5 including electrolyte additives selected from the group consisting of: SEI forming additives, cathode protecting agents, salt stabilizers, overcharge protecting additives, lithium depositing additives, salvation enhancers, corrosion inhibitors and wetting agents.

12. The organic electrolytic solution of claim 11 wherein the SEI forming additives are selected from the group consisting of: vinylene carbonate, vinyl ethylene carbonate, ethylene carbonate, allyl ethyl carbonate, vinyl acetate, divinyl adipate, acrylic acid nitrile, 2-vinyl pyridine, maleic anhydride, maleimides, methyl cinnamate, phosphonate, vinyl-containing silane-based compounds, furan derivatives that contain two double bonds in each molecule, sulfur-based compounds, including $SO_2$, polysulfide, cyclic alkyl sulfites, aryl sulfites, nitrates, nitrites, halogenated ethylene carbonate, halogenated lactone, methyl chloroformate, carboxyl phenol, aromatic esters, anhydrides, succinimide, N-benzyloxy carbonyloxy succinimide, aromatic isocyanates, $B_2O_3$, organic borates, boroxine compounds, halogenated organic compounds, polydimethylsiloxane, silanes, and tris(pentafluorophenyl) borane.

13. The organic electrolyte solution of claim 11 wherein the cathode protecting agents are selected from the group consisting of: amine-based organic bases such as butylamine, carbodiimide based compounds such as N, N-dicyclohexyl-carbodiimide, and N,N-diethylamino trimethylsilane.

14. The organic electrolyte solution of claim 11 wherein the salt stabilizers are selected from the group consisting of: LiF, Lewis bases including tris(2,2,2-trifluoroethyl) phosphate, amide-based compounds including 1-methyl-2-pyrrolidinone, fluorinated carbamate and hexamethyl-phosphoramide.

15. The organic electrolyte solution of claim 11 wherein the overcharge protecting additives are selected from the group consisting of: metallocenes, tetracyanoethylene, tetramethylphenylenediamine, dihydrophenazine derivatives bearing either 2-hydroxypropyl or ethyl substituents on both N atoms, substituted aromatic or heterocyclic compounds and their alkali metal salts, anisole-family compounds, 2,5-ditert-butyl-1,4-dimethoxybenzene, monomethoxy benzene class compounds, hexaethyl benzene, bipyridyl or biphenyl carbonates, difluoroanisoles, S- or N-containing heterocyclic aromatic compounds such as thianthrene and 2,7-diacetyl thianthrene, phenothiazinebased compounds, lithium fluorododecaborates, xylene, cyclohexylbenzene, biphenyl, 2,2-diphenylpropane, phenyl-tert-butyl carbonate, phenyl-R-phenyl compounds, 3-thiopheneacetonitrile, heterocyclic compounds including furan, thiophene, and N-methylpyrrole, 3,4-ethylenedioxythiophene, and LiBOB.

16. The organic electrolyte solution of claim 11 wherein the lithium depositing additives are selected from the group consisting of: $SO_2$ compounds, polysulfide, water, 2-methyltetrahydrofuran, 2-methylthiophene, nitromethane, tetraalkylammonium chlorides with a long alkyl chain, cetyltrimethylammonium chlorides, lithium and tetraethylammonium salts of perfluorooctanesulfonate, perfluoropolyethers, nitrile sucrose, nitrile cellulose, $AlI_3$, $SnI$, HF, and fluoroethylene carbonate.

17. The organic electrolyte solution of claim 11 wherein the salvation enhancers are selected from the group consisting of: as borate, borane, and borole compounds.

18. The organic electrolyte solution of claim 11 wherein the corrosion inhibitors and wetting agents are selected from the group consisting of: LiBOB, LiODFB, ionic and non-ionic surfactants, cyclohexane, trialkyl phosphate, linear esters with high molecular weight including methyl decanoate and dodecyl acetate, tertiary carboxylic acids, and $P_2O_5$.

19. A battery comprising:
a cathode;
an anode;
an organic electrolyte solvent including a compound of the formula:

$R_1$ is selected from alkyls, alkenyls, alkynyls, aryls and substituted fluorine derivatives that are partially or fully fluorinated of the alkyls, alkenyls, alkynyls and aryls of $R_1$; $R_2$ is selected from alkyls, alkenyls, alkynyls, aryls and substituted fluorine derivatives of the of the alkyls, alkenyls, alkynyls and aryls of $R_2$; $R_3$ is selected from alkyls, alkenyls, alkynyls, aryls and substituted fluorine derivatives of the alkyls, alkenyls, alkynyls and aryls of $R_3$ wherein when $R_1$, $R_2$, or $R_3$ is an alkyl, the alkyl has from 1 to 5 carbons; and an electrolyte salt dissolved in the organic electrolyte wherein the battery is stable at voltages of greater than 4.0 volts.

20. The battery of claim 19 including additional solvents selected from organic carbonates, ionic liquids, silanes and sulfones.

21. The battery of claim 19 wherein $R_1$ is a substituted fluorine derivatives of the alkyls, alkenyls, alkynyls and aryls of $R_1$ synthesized by electrochemical fluorination.

22. The battery of claim 19 wherein R1 is a substituted fluorine derivatives of the alkyls, alkenyls, alkynyls and aryls of $R_1$ synthesized by direct fluorination.

23. The battery of claim 19 wherein the electrolyte salt is selected from the group consisting of: $LiPF_6$, $LiAsF_6$, $LiSbF_6$, $LiBF_4$, $LiClO_4$, $LiCF_3SO_3$, $Li(CF_3SO_2)_2N$, $Li(C_2F_5SO_2)_2N$, $LiC_4F_9SO_3$, $Li(CF_3SO_2)_3C$, $LiBPh_4$ wherein Ph is phenyl, LiBOB, $Li(CF_3SO_2)(CF_3CO)N$ and combinations thereof.

24. The battery of claim 19 wherein the electrolyte salt has a concentration of from 0.5M to 3.0M.

25. The battery of claim 19 including electrolyte additives selected from the group consisting of: SEI forming additives, cathode protecting agents, salt stabilizers, overcharge protecting additives, lithium depositing additives, and salvation enhancers, corrosion inhibitors and wetting agents.

26. The battery of claim 19 wherein $R_1$, $R_2$ and $R_3$ are selected from linear alkyl, branched alkyl, partially fluorinated alkyl, and fully fluorinated alkyl groups.

* * * * *

UNITED STATES PATENT AND TRADEMARK OFFICE
CERTIFICATE OF CORRECTION

PATENT NO. : 8,288,040 B2  Page 1 of 1
APPLICATION NO. : 12/371979
DATED : October 16, 2012
INVENTOR(S) : John Muldoon et al.

It is certified that error appears in the above-identified patent and that said Letters Patent is hereby corrected as shown below:

In the Specification:

At column 4, line number 21, After cesium, Insert --.--.

In the Claims:

At column 8, claim number 19, line number 33, Delete second occurrence "of the".

Signed and Sealed this
Twenty-sixth Day of August, 2014

Michelle K. Lee
*Deputy Director of the United States Patent and Trademark Office*